United States Patent [19]
Andersen et al.

[11] Patent Number: 6,069,000
[45] Date of Patent: May 30, 2000

[54] ENZYME WITH PECTIN ESTERASE ACTIVITY

[75] Inventors: Lene Nonboe Andersen, Allerød; Markus Kauppinen, København; Gitte Budolfsen, Frederiksberg, all of Denmark

[73] Assignee: Novo Nordisk A/S, Bagsværd, Germany

[21] Appl. No.: 09/136,628

[22] Filed: Aug. 19, 1998

Related U.S. Application Data

[63] Continuation of application No. PCT/DK97/00073, Feb. 18, 1997.

[30] Foreign Application Priority Data

Feb. 21, 1996 [DK] Denmark .................................. 0191/96

[51] Int. Cl.$^7$ ................................ C12N 9/18; C12N 1/12; C12N 1/20; C12N 1/14; C07H 21/04
[52] U.S. Cl. .................... 435/197; 435/252.1; 435/252.3; 435/252.7; 435/252.33; 435/253.3; 435/254.3; 435/254.6; 435/254.7; 435/254.11; 435/254.21; 435/255.2; 435/256.1; 435/320.1; 536/23.2
[58] Field of Search ................................ 435/197, 252.3, 435/252.33, 320.1, 256.1, 255.2, 252.1, 252.7, 253.3, 254.11, 254.7, 254.3, 254.21, 254.6; 536/23.2

[56] References Cited

U.S. PATENT DOCUMENTS 4,200,694   4/1980   Shigetaka et al. ...................... 435/101

FOREIGN PATENT DOCUMENTS

WO 94/25575   11/1994   Denmark .
0388593   9/1990   Germany .

OTHER PUBLICATIONS

Khanh et al. (1990) Nucleic Acids Research 18(14):4262.
Dudchenko, Chemical Abstracts, Accession No. 202881q, 104(23):353.
Dialog Information Services, File 5, BIOSIS. Accession No. 10020821.
Dialog Information Services, File 5, BIOSIS. Accession No. 2458386.
EMBL, Database GenBank/DDBJ, Anpecase Accession No. X52902.
Markovic et al. (1989) Biologia 44(12):1185–1189.
Tierny et al. (1994) Journal of Applied Bacteriology 76:592–602.
Laurent et al. (1993) Gene 131:17–25.
Plastow (1988) Molecular Microbiology 2(2):247–254.
Spök et al. (1991) Journal of General Microbiology 137:131–140.
Khanh et al. (1991) Gene 106:71–77.

*Primary Examiner*—Ponnathapu Achutamurthy
*Assistant Examiner*—Elizabeth Slobodyansky
*Attorney, Agent, or Firm*—Steve T. Zelson, Esq.; Reza Green, Esq.

[57] ABSTRACT

The present invention relates to an enzyme with pectin esterase activity, a DNA construct encoding the enzyme with pectin esterase activity, a method of producing the enzyme, an enzyme composition comprising said enzyme with pectin esterase activity, and the use of said enzyme and enzyme composition for a number of industrial applications.

16 Claims, No Drawings

ENZYME WITH PECTIN ESTERASE ACTIVITY

CROSS-REFERENCE TO RELATED APPLICATIONS

This application is a continuation of PCT/DK97/00073 filed Feb. 18, 1997, and claims priority under 35 U.S.C. 119 of Danish application 0191/96, filed Feb. 21, 1997, the contents of which are fully incorporated herein by reference.

FIELD OF INVENTION

The present invention relates to an enzyme with pectin esterase activity, a DNA construct encoding the enzyme with pectin esterase activity, a method of producing the enzyme, an enzyme composition comprising said enzyme with pectin esterase activity, and the use of said enzyme and enzyme composition for a number of industrial applications.

BACKGROUND OF THE INVENTION

Pectin polymers are important constituents of plant primary cell walls. They are composed of chains of 1,4-linked α-D-galacturonic acid and methylated derivatives thereof. The use of pectin-degrading enzymes such as polygalacturonase, pectin methylesterase, pectin lyase or pectate lyase is important for the food industry, primarily in fruit and vegetable processing such as fruit juice production or wine making, where their ability to catalyse the degradation of the backbone of the pectin polymer is utilised.

For many purposes, it would be desirable to provide each of the pectin degrading enzymes present in, for instance, commercial preparations containing a number of different pectin degrading enzymes (an example of such a preparation is Pectinex Ultra SP®, prepared from *Aspergillus aculeatus*, available from Novo Nordisk A/S) in a form free from other components. In this way, it would be possible to produce enzyme preparations adapted to specific purposes, such preparations either containing a single pectin degrading enzyme or arbitrary combinations thereof. To serve this end, it is convenient to provide single-component pectin degrading enzymes by recombinant DNA techniques.

Pectin methylesterase (EC 3.1.1.11) catalyses the removal of methanol from pectin, resulting in the formation of pectic acid (polygalacturonic acid).

Pectin methylesterases are produced by a number of microorganisms and have also been found to be present in leaves, roots, stalks and fruits of many higher plants. Microbial pectin methylesterases have been cloned by Khanh et al. (1990) "Nucleotide and derived amino acid sequence of a pectinesterase cDNA isolated from *Aspergillus niger* strain RH5344", Nucleic Acids Res. 18:4262; Khanh et al. (1991) "Characterization and expression of a genomic pectin methyl esterase-encoding gene in *Aspergillus niger*", Gene 106:71–77; Spok et al. (1991) "Molecular cloning and sequencing of a pectinesterase gene from *Pseudomonas solanacearum*", J. Gen. Microbiol. 137:131–140; Plastow (1988) "Molecular cloning and nucleotide sequence of the pectin methyl esterase gene of *Erwinia chrysanthemi* B374", Mol. Microbiol. 2:247–254; Laurent et al. (1993) "Characterization and overexpression of the pem gene encoding pectin methylesterase of *Erwinia chrysanthemi* strain 3937", Gene 131:17–25; Tierny et al. (1994) "Molecular cloning and expression in *Escherichia coli* of genes encoding pectate lyase and pectin methylesterase activities from *Bacteroides thetaiotaomicron*", J. Appl. Bacteriol. 76:592–602.

WO 94/25575 describes the cloning of a pectin methyl-esterase from *Aspergillus aculeatus*.

SUMMARY OF THE INVENTION

According to the present invention, the inventors have now succeeded in isolating and characterizing a DNA sequence, from a Basidiomycota fungus, which encodes an enzyme exhibiting pectin methylesterase also known as pectin esterase activity, thereby making it possible to prepare a mono-component pectin esterase composition.

Accordingly, in a first aspect the invention relates to a DNA construct comprising a DNA sequence encoding an enzyme exhibiting pectin esterase activity, which DNA sequence comprises
  a) the pectin esterase encoding part of the DNA sequence cloned into plasmid pYES 2.0 present in *E. coli* DSM 10357, or
  b) an analogue of the DNA sequence defined in a) which
    i) is at least 60% homologous with the DNA sequence defined in a), or
    ii) hybridizes with the DNA sequence shown in positions 4–933 in SEQ ID NO 1 at low stringency, or
    iii) encodes a polypeptide which is at least 50% homologous with the polypeptide encoded by a DNA sequence comprising the DNA sequence defined in a), or
    iv) encodes a polypeptide which is immunologically reactive with an antibody raised against the purified pectin esterase encoded by the DNA sequence defined in a).

The full length cDNA sequence encoding a pectin esterase has been derived from a strain of the filamentous fungus *Meripilus giganteus* and has been cloned into plasmid pYES 2.0 present in the *Escherichia coli* strain DSM No. 10357.

Said pectin esterase encoding DNA sequence harboured in *E. coli* DSM 10357 is believed to have the same sequence as that presented in SEQ ID NO 1. Accordingly, whenever reference is made to the pectin esterase encoding part of the DNA sequence cloned into plasmid pYES 2.0 present in DSM 10357 such reference is also intended to include the pectin esterase encoding part of the DNA sequence presented in SEQ ID NO 1.

Accordingly, the terms "the pectin esterase encoding part of the DNA sequence cloned into plasmid pYES 2.0 present in DSM 10357" and "the pectin esterase encoding part of the DNA sequence presented in SEQ ID NO 1" may be used interchangeably.

In further aspects the invention provides an expression vector harbouring the DNA construct of the invention, a cell comprising said DNA construct or said expression vector and a method of producing an enzyme exhibiting pectin esterase activity, which method comprises culturing said cell under conditions permitting the production of the enzyme, and recovering the enzyme from the culture.

In a still further aspect the invention provides an enzyme exhibiting pectin esterase activity, which enzyme,
  (a) is encoded by a DNA construct of the invention; or
  (b) is produced by the method of the invention; and/or
  (c) is immunologically reactive with an antibody raised against a purified pectin esterase encoded by the pectin esterase encoding part of the DNA sequence cloned into plasmid pYES 2.0 present in *E. coli* DSM 10357. In a preferred embodiment the enzyme has the deduced amino acid sequence SEQ ID NO 2.

In a still further aspect, the present invention provides an enzyme composition useful for the degradation or modification of plant material or components thereof, said composition being enriched with an enzyme exhibiting pectin esterase activity as described above.

In a still further aspect, the present invention relates to the use of an enzyme or an enzyme composition of the invention for various industrial applications.

Finally the invention relates to an isolated substantially pure biological culture of the E. coli strain DSM No. 10357 harbouring a pectin esterase encoding DNA sequence (the pectin esterase encoding part of the DNA sequence cloned into plasmid pYES 2.0 present in E. coli DSM 10357) derived from a strain of the filamentous fungus *Meripilus giganteus*, or any mutant of said E. coli strain having retained the pectin esterase encoding capability; and to an isolated substantially pure biological culture of the filamentous fungus *Meripilus giganteus* CBS No. 521.95, from which the DNA sequence presented as SEQ ID No. 1 has been derived.

DETAILED DESCRIPTION OF THE INVENTION

DNA Constructs

The present invention provides a DNA construct comprising a DNA sequence encoding an enzyme exhibiting pectin esterase activity, which DNA sequence comprises
a) the pectin esterase encoding part of the DNA sequence cloned into plasmid pYES 2.0 present in E. coli DSM 10357, or
b) an analogue of the DNA sequence defined in a) which
   i) is at least 60% homologous with the DNA sequence defined in a), or
   ii) hybridizes with the DNA sequence shown in positions 4–933 in SEQ ID NO 1 at low stringency, or
   iii) encodes a polypeptide which is at least 50% homologous with the polypeptide encoded by a DNA sequence comprising the DNA sequence defined in a), or
   iv) encodes a polypeptide which is immunologically reactive with an antibody raised against the purified pectin esterase encoded by the DNA sequence defined in a).

As defined herein, a DNA sequence analogous to the pectin esterase encoding part of the DNA sequence cloned into plasmid pYES 2.0 present in E. coli DSM 10357 is intended to indicate any DNA sequence encoding an enzyme exhibiting pectin esterase activity, which enzyme has one or more of the properties cited under (i)–(iv) above.

The analogous DNA sequence may be isolated from a strain of the filamentous fungus *Meripilus giganteus* producing the enzyme with pectin esterase activity, or another or related organism and thus, e.g. be an allelic or species variant of the pectin esterase encoding part of the DNA sequence cloned into plasmid pYES 2.0 present in E. coli DSM 10357.

Alternatively, the analogous sequence may be constructed on the basis of the DNA sequence presented as the pectin esterase encoding part of SEQ ID No. 1, e.g be a subsequence thereof, and/or by introduction of nucleotide substitutions which do not give rise to another amino acid sequence of the pectin esterase encoded by the DNA sequence, but which corresponds to the codon usage of the host organism intended for production of the enzyme, or by introduction of nucleotide substitutions which may give rise to a different amino acid sequence.

When carrying out nucleotide substitutions, amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain.

Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine). For a general description of nucleotide substitution, see e.g. Ford et al., (1991), Protein Expression and Purification 2, 95–107.

It will be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (cf. e.g. Cunningham and Wells, (1989), Science 244, 1081–1085). In the latter technique mutations are introduced at every residue in the molecule, and the resultant mutant molecules are tested for biological (i.e. pectin esterase) activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labelling (cf. e.g. de Vos et al., (1992), Science 255, 306–312; Smith et al., (1992), J. Mol. Biol. 224, 899–904; Wlodaver et al., (1992), FEBS Lett. 309, 59–64).

The homology referred to in i) above is determined as the degree of identity between the two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., U.S.A. 53711) (Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3, the coding region of the DNA sequence exhibits a degree of identity preferably of at least 60%, more preferably at least 70%, more preferably at least 80%, more preferably at least 90%, more preferably at least 95%, and even more preferably at least 97%, with the pectin esterase encoding part of the DNA sequence shown in SEQ ID No. 1.

The hybridization referred to in (ii) above is intended to indicate that the analogous DNA sequence hybridizes to the same probe as the DNA sequence encoding the pectin esterase enzyme under certain specified conditions which are described in detail in the Materials and Methods section hereinafter. The oligonucleotide probe to be used is the DNA sequence corresponding to the pectin esterase encoding part of the DNA sequence shown in SEQ ID NO 1.

The homology referred to in iii) above is determined as the degree of identity between the two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., U.S.A. 53711) (Needleman, S. B. and Wunsch, C. D., (1970), Journal of Molecular Biology, 48, 443–453. Using GAP with the following settings for polypeptide sequence comparison: GAP creation penalty of 3.0 and GAP extension penalty of 0.1, the polypeptide encoded by an analogous DNA sequence exhibits a degree of identity preferably of at least 50%, more preferably at least 60%, more preferably at least 70%, more preferably at least 80%, more preferably at least 90%, more preferably at least 95%, and especially at least 97% with the enzyme encoded by a DNA construct comprising the pectin esterase encoding part of the DNA sequence shown in SEQ ID No. 1, e.g. with the amino acid sequence SEQ ID NO 2.

The present invention is also directed to pectin more than two amino acids, and more preferably by no more than one amino acid from the mature part of the amino acid sequence set forth in SEQ ID NO 2.

In connection with property iv) the immunological reactivity may be determined by the method described in the Materials and Methods section below.

The DNA sequence encoding a pectin esterase of the invention can be isolated from the strain *Escherichia coli* DSM 10357 using standard methods e.g. as described by Sambrook et al., (1989), Molecular Cloning: A Laboratory Manual. Cold Spring Harbor Lab.; Cold Spring Harbor, N.Y.

The DNA sequence encoding an enzyme exhibiting pectin esterase activity of the invention can also be isolated by any general method involving cloning, in suitable vectors, a cDNA library from any organism expected to produce the pectin esterase of interest, transforming suitable yeast host cells with said vectors, culturing the host cells under suitable conditions to express any enzyme of interest encoded by a clone in the cDNA library, screening for positive clones by determining any pectin esterase activity of the enzyme produced by such clones, and isolating the enzyme encoding DNA from such clones.

A general isolation method has been disclosed in WO 93/11249 or WO 94/14953, the contents of which are hereby incorporated by reference. A more detailed description of the screening method is given in Example 1 below.

Alternatively, the DNA encoding a pectin esterase of the invention may, in accordance with well-known procedures, conveniently be isolated from a suitable source, such as any of the below mentioned organisms, by use of synthetic oligonucleotide probes prepared on the basis of a DNA sequence disclosed herein. For instance, a suitable oligonucleotide probe may be prepared on the basis of the pectin esterase encoding part of the nucleotide sequences presented as SEQ ID No. 1 or any suitable subsequence thereof, or the basis of the amino acid sequence SEQ ID NO 2.

Microbial Sources

In a preferred embodiment, the DNA sequence encoding the pectin esterase is derived from a strain belonging to the Polyporaceae family, which according to the entrez browser NCBI taxonomy version 3,3, (updated Dec. 13, 1995) is a family within the order Aphyllophorales, which belongs to the class of Hymenomycetes under the Basidiomycota.

It is at present contemplated that a DNA sequence encoding an enzyme homologous to the enzyme of the invention, i.e. an analogous DNA sequence, may be obtained from other microorganisms. For instance, the DNA sequence may be derived by similarly screening a cDNA library of another microorganism, such as a strain of Aspergillus, Saccharomyces, Bacteroides, Erwinia, Pseudomonas or Clostridium.

An isolate of a strain of *Meripilus giganteus* from which a pectin esterase of the invention can be derived has been deposited by the inventors according to the Budapest Treaty on the International Recognition of the Deposit of Microorganisms for the Purposes of Patent Procedure at the Centraalbureau voor Schimmelcultures, P.O. Box 273, 3740 AG Baarn, The Netherlands (CBS).

Deposit date: 04.07.95

Depositor's ref.: NN006040

CBS designation: *Meripilus giganteus* CBS No. 521.95

The expression plasmid pYES 2.0 comprising the full length cDNA sequence encoding the pectin esterase of the invention has been transformed into a strain of the *E. coli* which was deposited by the inventors according to the Budapest Treaty on the International Recognition of the Deposit of Microorganisms for the Purposes of Patent Procedure at the Deutshe Sammlung von Mikroorganismen und Zellkulturen GmbH., Masheroder Weg 1b, D-38124 Raunschweig, Federal Republic of Germany, (DSM).

Deposit date: 06.12.95

Depositor's ref.: NN049144

DSM designation: *Escherichia coli* DSM 10357

Expression Vectors

In another aspect, the invention provides a recombinant expression vector comprising the DNA construct of the invention.

The expression vector of the invention may be any expression vector that is conveniently subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the expression vector, the DNA sequence encoding the pectin esterase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the pectin esterase, the promoter and the terminator, respectively, and to insert them into suitable vectors are well known to persons skilled in the art (cf., for instance, Sambrook et al., (1989), Molecular Cloning. A Laboratory Manual, Cold Spring Harbor, N.Y.).

Examples of suitable promoters for use in filamentous fungus host cells are, for instance, the ADH3 promoter (McKnight et al., *The EMBO J.* 4 (1985), 2093–2099) or the tpiA promoter. Examples of other useful promoters are those derived from the gene encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (gluA), *Rhizomucor miehei* lipase, *Aspergillus oryzae* alkaline protease, *Aspergillus oryzae* triose phosphate isomerase or *Aspergillus nidulans* acetamidase.

Host Cells

In yet another aspect the invention provides a host cell comprising the DNA construct of the invention and/or the recombinant expression vector of the invention.

Preferably, the host cell of the invention is a eukaryotic cell, in particular a fungal cell such as a yeast or filamentous fungal cell. In particular, the cell may belong to a species of Trichoderma, preferably *Trichoderma harzianum* or *Trichoderma reesei*, or a species of Aspergillus, most preferably *Aspergillus oryzae* or *Aspergillus niger*, or a species of Fusarium, in particular a strain of *Fusarium graminearum*, *Fusarium cerealis*. Fungal cells may be transformed by a process involving protoplast formation and transformation of the protoplasts followed by regeneration of the cell wall in a manner known per se. The use of Aspergillus as a host microorganism is described in EP 238 023 (Novo Nordisk A/S), the contents of which are hereby incorporated by reference. The host cell may also be a yeast cell, e.g. a strain of Saccharomyces, in particular *Saccharomyces cerevisae*, *Saccharomyces kluyveri* or *Saccharomyces uvarum*, a strain of Schizosaccharomyces sp., such as *Schizosaccharomyces pombe,* a strain of Hansenula sp., Pichia sp., Yarrowia sp., such as *Yarrowia lipolytica,* or Kluyveromyces sp., such as *Kluyveromyces lactis.*

Method of Producing Pectin Esterase

In a still further aspect, the present invention provides a method of producing an enzyme according to the invention, wherein a suitable host cell, which has been transformed with a DNA sequence encoding the enzyme, is cultured under conditions permitting the production of the enzyme, and the resulting enzyme is recovered from the culture.

The medium used to culture the transformed host cells may be any conventional medium suitable for growing the host cells in question. The expressed pectin esterase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Enzyme Compositions

In a still further aspect, the present invention relates to an enzyme composition useful for the modification or degradation of plant cell wall components, said composition being enriched in an enzyme exhibiting pectin esterase activity as described above.

The enzyme composition having been enriched with an enzyme of the invention may e.g. be an enzyme composition comprising multiple enzymatic activities, in particular an enzyme composition comprising multiple plant cell wall degrading enzymes such as Viscozym®, Pectinex® or Pectinex Ultra SP® (all available from Novo Nordisk A/S). In this manner a boosting of the cell wall degrading ability of the enzyme composition can be obtained.

In the present context, the term "enriched" is intended to indicate that the pectin esterase activity of the enzyme composition has been increased, e.g. with an enrichment factor of 1.1, conveniently due to addition of an enzyme of the invention prepared by the method described above.

Alternatively, the enzyme composition enriched in an enzyme exhibiting pectin esterase activity may be one which comprises an enzyme of the invention as the major enzymatic component, e.g. a mono-component enzyme composition.

The enzyme composition may be prepared in accordance with methods known in the art and may be in the form of a liquid or a dry composition. For instance, the enzyme composition may be in the form of a granulate or a microgranulate. The enzyme to be included in the composition may be stabilized in accordance with methods known in the art.

Examples are given below of preferred uses of the enzyme composition of the invention. The dosage of the enzyme composition of the invention and other conditions under which the composition is used may be determined on the basis of methods known in the art.

The enzyme composition according to the invention may be useful for at least one of the following purposes.

Degradation or Modification of Plant Material

The enzyme composition may advantageously be used for the treatment of pectin containing plant material, e.g. of vegetable or fruit origin, such as material obtained from soy beans, sugar beets or apples, so as to reduce the viscosity and thus improve the processing or appearance of the plant material in question. The viscosity reduction may be obtained by treating the pectin-containing plant material with an enzyme preparation of the invention under suitable conditions for full or partial degradation of the pectin-containing material.

The enzyme composition may be used for de-pectinization and viscosity reduction in vegetable or fruit juice, especially in apple or pear juice.

The enzyme preparation may be used in the treatment of mash from fruits and vegetables, for instance in the mash treatment of apples and pears for juice production, and in the mash treatment of grapes for wine production.

The enzyme composition may be used in the production of citrus juice, e.g. for partial or complete degradation of the pulp present in the juice after pressing.

For the above uses it is preferred that the enzyme composition in addition to pectin esterase comprises a polygalacturonase containing enzyme preparation.

By use of an enzyme preparation of the invention it is possible to regulate the consistency and appearance of processed fruit or vegetables. Thus, the consistency and appearance have been found to be a product of the actual combination of enzymes used for the processing, i.e. the nature of the enzymes (especially pectin degrading enzyme (s)) with which the pectin methylesterase of the invention is combined.

Examples of products with specific properties which may be produced by use of an enzyme preparation of the invention include clear juice from apples, pears or berries, cloud stable juice from apples, pears, berries, citrus, or tomatoes, and purees from carrots and tomatoes.

From the foregoing disclosure it will be apparent that the pectinesterase of the invention may be produced as a single component essentially free from other enzyme activities such as polygalacturonase and/or pectin lyase activity normally found to be present in commercially available pectinesterase containing pectinolytic preparations.

On this basis the use of the pectin esterase of the invention is especially advantageous for purposes in which the action of such other enzyme activities is undesirable.

Examples of such purposes include the use af the pectin methylesterase for full or partial demethylation of pectin in processed or non-processed fruits and vegetables.

The partial demethylation is, e.g., important when an improved firmness of fruits or vegetables is desirable. Thus, firmness is often reduced during processing (e.g. canning and pasteurization). By use of a controlled amount of a pectin esterase of the invention a partial demethylation of pectin present in the fruits and vegetables may be obtained and the resulting partially demethylated pectin may crosslink with, e.g., divalent ions such as calcium, whereby a more firm fruits or vegetables may be formed. Accordingly, the pectin esterase of the invention may be used for improving the firmness of, e.g., red and green pepper, beans, peas and sliced fruits such as pears and apples.

Infusion of the enzyme can be performed e.g. unassisted by immersion or assisted by vacuum threatment.

Another example of the purposes is demethylation of pectin, e.g. from citrus, apple, sunflower and/or sugar beet.

Furthermore, the pectin esterase can be used to obtain an in situ viscosity increase or gel formation in various vegetable or fruit based products.

The pectin esterase of the invention can alone or together with other enzymes be used to improve the digestibility of pectin containing animal feed, e.g. feed prepared from soya beans, sugar beets or rape seeds. For this purpose, an enzyme composition of the invention is added to the feed.

The pectin esterase activity can together with other enzymes be used to produce monogalacturonic acid or galacturonic acid containing oligosaccharides from pectin-containing material such as sugar beet pulp in accordance with well-known methods. Monogalacturonic acid may be used for production of galactaric acid or for production of fatty acid and fatty alcohol esters and/or ethers of galacturonic acid. Galacturonic containing oligosaccharides may be used as additives for human food or animal feed.

Furthermore, the pectin esterase can in combination with other enzymes be used for the removal of pectic substances from plant fibres, which removal is essential, e.g. in the production of textile fibres or other cellulosic materials. For this purpose plant fibre material is treated with a suitable amount of the pectin esterase of the invention under suitable conditions for obtaining full or partial degradation of pectic substances associated with the plant fibre material.

Mode of Action Block-wise vs Random Cleavage

The distribution of the carboxyl groups in pectin is of importance for the functional properties of the pectin.

Several methods to determine the distribution of the free carboxyl groups on pectin have been described (Grasdalen, H. et al, *Carbohydrate Res.*, 289, 105 (1995)). With the aim of characterizing the mode of action of a pectin esterase the distribution of the acid groups is determined by a method described by Mort et al. (Mort, A. J. et al, *Carbohyd. Res.*, 247, 21 (1993)). The esterified galacturonic acids are converted to galactose by reduction with sodium borohydride. Subsequently the glycosidic linkages of the resulting galactose residues are cleaved selectively by HF solvolysis. This leads to the production of oligomers: (Gal A)$_n$–Gal. These oligomers represent the contiguous stretches of Gal A residues between methyl-esterified residues in the pectin. The cloned esterase of the invention was compared to an orange esterase and to alkaline treatment. By high-performance anion exchange chromatography oligomers of six galacturonic acid residues were separated and quantified. From the distribution of these oligomers it can be determined whether the acid groups in the pectin are randomly or blockwise distributed.

Grasdalen et al, 1995 describes NMR spectroscopy as a useful method to obtain quantitative information on the composition and the sequential structure of pectin. Contrary to the method defined by Mort et al 1993 NMR spectroscopy represents a direct approach to verify sequential structure, and only a moderate degree of polymer degradation is needed.

Without being bound to any theory, it is presently believed that the improved performance of the pectin esterase of the invention for a number of industrial applications such as in gelatination of jam (see Example 4 herein), is due to the mode of action of the enzyme of the invention preferably providing a block-wise distribution of the acid groups in the pectin.

The invention is described in further detail in the following examples which are not in any way intended to limit the scope of the invention as claimed.

MATERIALS AND METHODS

Deposited Organisms

*Meripilus giganteus* CBS 521.95 comprises the pectin esterase encoding DNA sequence of the invention.

*Escherichia coli* DSM 10357 containing the plasmid comprising the full length cDNA sequence, coding for the pectin esterase of the invention, in the shuttle vector pYES 2.0.

Other Strains

Yeast strain: The *Saccharomyces cerevisiae* strain used was W3124 (MATα; ura 3–52; leu 2–3, 112; his 3–D200; pep 4–1137; prc1::HIS3; prb1:: LEU2; cir+).

*E. coli* strain: DH10B (Life Technologies)

Plasmids

The Aspergillus expression vector pHD414 is a derivative of the plasmid p775 (described in EP 238 023). The construction of pHD414 is further described in WO 93/11249.

pYES 2.0 (Invitrogen)

pA2PE18 (See example 1)

Extraction of total RNA is performed with guanidinium thiocyanate followed by ultracentrifugation through a 5.7 M CsCl cushion, and isolation of poly(A)$^+$RNA is carried out by oligo(dT)-cellulose affinity chromatography using the procedures described in WO 94/14953.

cDNA Synthesis

Double-stranded cDNA is synthesized from 5 μg poly (A)$^+$RNA by the RNase H method (Gubler and Hoffman (1983) Gene 25:263–269, Sambrook et al. (1989) Molecular cloning: A laboratory manual, Cold Spring Harbor lab., Cold Spring Harbor, N.Y.) using the hair-pin modification developed by F. S. Hagen (pers. comm.). The poly(A)$^+$RNA (5 μg in 5 μl of DEPC-treated water) is heated at 70° C. for 8 min. in a pre-siliconized, RNase-free Eppendorph tube, quenched on ice and combined in a final volume of 50 μl with reverse transcriptase buffer (50 mM Tris-Cl, pH 8.3, 75 mM KCl, 3 mM MgCl$_2$, 10 mM DTT, Bethesda Research Laboratories) containing 1 mM of DATP, dGTP and dTTP and 0.5 mM 5-methyl-dCTP (Pharmacia), 40 units human placental ribonuclease inhibitor (RNasin, Promega), 1.45 μg of oligo(dT)$_{18}$-Not I primer (Pharmacia) and 1000 units SuperScript II RNase H reverse transcriptase (Bethesda Research Laboratories). First-strand cDNA is synthesized by incubating the reaction mixture at 45° C. for 1 hour. After synthesis, the mRNA:cDNA hybrid mixture is gelfiltrated through a MicroSpin S-400 HR (Pharmacia) spin column according to the manufacturer's instructions.

After the gelfiltration, the hybrids are diluted in 250 μl second strand buffer (20 mM Tris-Cl, pH 7.4, 90 mM KCl, 4.6 mM $MgCl_2$, 10 mM $(NH_4)_2SO_4$, 0.16 mM βNAD+) containing 200 μM of each dNTP, 60 units *E. coli* DNA polymerase I (Pharmacia), 5.25 units RNase H (Promega) and 15 units *E. coli* DNA ligase (Boehringer Mannheim). Second strand cDNA synthesis is performed by incubating the reaction tube at 16° C. for 2 hours and additional 15 min. at 25° C. The reaction is stopped by addition of EDTA to a final concentration of 20 mM followed by phenol and chloroform extractions.

Mung Bean Nuclease Treatment

The double-stranded cDNA is precipitated at −20° C. for 12 hours by addition of 2 vols 96% EtOH, 0.2 vol 10 M $NH_4Ac$, recovered by centrifugation, washed in 70% EtOH, dried and resuspended in 30 μl Mung bean nuclease buffer (30 mM NaAc, pH 4.6, 300 mM NaCl, 1 mM $ZnSO_4$, 0.35 mM DTT, 2% glycerol) containing 25 units Mung bean nuclease (Pharmacia). The single-stranded hair-pin DNA is clipped by incubating the reaction at 30° C. for 30 min., followed by addition of 70 μl 10 mM Tris-Cl, pH 7.5, 1 mM EDTA, phenol extraction and precipitation with 2 vols of 96% EtOH and 0.1 vol 3 M NaAc, pH 5.2 on ice for 30 min.

Blunt-ending with T4 DNA Polymerase

The double-stranded cDNAs are recovered by centrifugation and blunt-ended in 30 μl T4 DNA polymerase buffer (20 mM Tris-acetate, pH 7.9, 10 mM MgAc, 50 mM KAc, 1 mM DTT) containing 0.5 mM of each DNTP and 5 units T4 DNA polymerase (New England Biolabs) by incubating the reaction mixture at 16° C. for 1 hour. The reaction is stopped by addition of EDTA to a final concentration of 20 mM, followed by phenol and chloroform extractions, and precipitation for 12 hours at −20° C. by adding 2 vols 96% EtOH and 0.1 vol 3 M NaAc pH 5.2.

Adaptor Ligation, Not I Digestion and Size Selection

After the fill-in reaction the cDNAs are recovered by centrifugation, washed in 70% EtOH and dried. The cDNA pellet is resuspended in 25 μl ligation buffer (30 mM Tris-Cl, pH 7.8, 10 mM $MgCl_2$, 10 mM DTT, 0.5 mM ATP) containing 2.5 μg non-palindromic BstXI adaptors (Invitrogen) and 30 units T4 ligase (Promega) and incubated at 16° C. for 12 hours. The reaction is stopped by heating at 65° C. for 20 min. and then cooling on ice for 5 min. The adapted cDNA is digested with Not I restriction enzyme by addition of 20 μl water, 5 μl 10×Not I restriction enzyme buffer (New England Biolabs) and 50 units Not I (New England Biolabs), followed by incubation for 2.5 hours at 37° C. The reaction is stopped by heating at 65° C. for 10 min. The cDNAs are size-fractionated by gel electrophoresis on a 0.8% SeaPlaque GTG low melting temperature agarose gel (FMC) in 1×TBE to separate unligated adaptors and small cDNAs. The cDNA is size-selected with a cut-off at 0.7 kb and rescued from the gel by use of β-Agarase (New England Biolabs) according to the manufacturer's instructions and precipitated for 12 hours at −20° C. by adding 2 vols 96% EtOH and 0.1 vol 3 M NaAc pH 5.2.

Construction of Libraries

The directional, size-selected cDNA is recovered by centrifugation, washed in 70% EtOH, dried and resuspended in 30 μl 10 mM Tris-Cl, pH 7.5, 1 mM EDTA. The cDNAs are desalted by gelfiltration through a MicroSpin S-300 HR (Pharmacia) spin column according to the manufacturer's instructions. Three test ligations are carried out in 10 μl ligation buffer (30 mM Tris-Cl, pH 7.8, 10 mM $MgCl_2$, 10 mM DTT, 0.5 mM ATP) containing 5 μl double-stranded cDNA (reaction tubes #1 and #2), 15 units T4 ligase (Promega) and 30 ng (tube #1), 40 ng (tube #2) and 40 ng (tube #3, the vector background control) of BstXI-NotI cleaved pYES 2.0 vector. The ligation reactions are performed by incubation at 16° C. for 12 hours, heating at 70° C. for 20 min. and addition of 10 μl water to each tube. 1 μl of each ligation mixture is electroporated into 40 μl electrocompetent *E. coli* DH10B cells (Bethesda research Laboratories) as described (Sambrook et al. (1989) Molecular cloning: A laboratory manual, Cold Spring Harbor lab., Cold Spring Harbor, N.Y.). Using the optimal conditions a library is established in *E. coli* consisting of pools. Each pool is made by spreading transformed *E. coli* on LB+ampicillin agar plates giving 15.000–30.000 colonies/plate after incubation at 37° C. for 24 hours. 20 ml LB+ampicillin is added to the plate and the cells were suspended herein. The cell suspension is shaked in a 50 ml tube for 1 hour at 37° C. Plasmid DNA is isolated from the cells according to the manufacturer's instructions using QIAGEN plasmid kit and stored at −20° C.

1 μl aliquots of purified plasmid DNA (100 ng/μl) from individual pools are transformed into *S. cerevisiae* W3124 by electroporation (Becker and Guarante (1991) Methods Enzymol. 194:182–187) and the transformants are plated on SC agar containing 2% glucose and incubated at 30° C.

Identification of Positive Clones

After 3–5 days of incubation, the SC agar plates were replica plated onto a set of SC+galactose agar plates. Those plates were incubated for 2–4 days at 30° C. and overlayered with a pectin overlayer gel, containing 1% apple pectin DE 75%, 1% HSB agarose in an appropriate buffer, for detection of pectinolytic activity. After incubation overnight at 30° C., 10–15 ml of a 1% solution of MTAB (mixed alkyltrimethylammonium bromide) was poured onto the overlayer and removed after 1 hour. Pectin methylesterase positive colonies were identified as colonies surrounded by a white halo.

Characterization of Positive Clones

The positive clones are obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al. (1977) Proc. Natl. Acad. Sci. U.S.A. 74:5463–5467) and the Sequenase system (United States Biochemical).

Isolation of a cDNA Gene for Expression in Aspergillus

A pectin esterase-producing yeast colony is inoculated into 20 ml YPD broth in a 50 ml glass test tube. The tube is shaken for 2 days at 30° C. The cells are harvested by centrifugation for 10 min. at 3000 rpm.

DNA is isolated according to WO 94/14953 and dissolved in 50 μl water. The DNA is transformed into *E. coli* by standard procedures. Plasmid DNA is isolated from *E. coli* using standard procedures, and analyzed by restriction enzyme analysis. The cDNA insert is excised using appropriate restriction enzymes and ligated into an Aspergillus expression vector.

Transformation of *Aspergillus oryzae* or *Aspergillus niger*

Protoplasts may be prepared as described in WO 95/02043, p. 16, line 21–page 17, line 12, which is hereby incorporated by reference.

100 µl of protoplast suspension is mixed with 5–25 µg of the appropriate DNA in 10 µl of STC (1.2 M sorbitol, 10 mM Tris-HCl, pH=7.5, 10 mM CaCl$_2$). Protoplasts are mixed with p3SR2 (an *A. nidulans* amdS gene carrying plasmid). The mixture is left at room temperature for 25 minutes. 0.2 ml of 60% PEG 4000 (BDH 29576), 10 mM CaCl$_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on minimal plates (Cove, Biochem. Biophys. Acta 113 (1966) 51–56) containing 1.0 M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of *A. oryzae* Transformants

Each of the transformants are inoculated in 10 ml of YPM (cf. below) and propagated. After 2–5 days of incubation at 30° C., the supernatant is removed. The pectin esterase activity is identified by applying 10 µl supernatant to 4 mm diameter holes punched out in an agarose gel containing 1% apple pectin DE 75%, incubation overnight at 30° C. and precipitation with MTAB as described above. Pectin esterase activity is then identified by a white halo.

Fed Batch Fermentation

Fermentations were carried out as fed-batch processes with maltodextrin as carbon source, urea as nitrogen source and yeast extract. The pH was maintained at 7.0 and the temperature was maintained at 34° C. during the entire process. After fermentation the pectin esterase was recovered by centrifugation and germ filtration.

Purification of the Enzyme

The recombinant pectin esterase from *A. oryzae* was purified as follows: A culture supernatant was harvested after 5 days of culture, and centrifuged, germ filtered, and ultrafiltrated on a 3 kDa cut-off Filtron cassette (Minisette) to minimal volume. 25 ml of the ultrafiltrate was dialysed with 50 mM H$_3$BO$_3$, 5 mM DMG, 1 mM CaCl$_2$, pH 7.0 and applied to a 40 ml Q-Sepharose FF column (Pharmacia, Sweden) equilibrated in the same buffer. After washing the column, bound protein was eluted with a linear NaCl gradient (from 0 to 0.5 M NaCl). Fractions from the column were analysed for pectin esterase activity by the apple pectin assay as described above. Most of the pectin esterase activity was seen in the run-through, whereas most of the protein bound to the column.

The pH of the run-through was adjusted to pH 4.5 with CH$_3$COOH and applied to a 50 ml S-Sepharose HP column (Pharmacia, Sweden) equilibrated in 25 mM CH$_3$COOH/NaOH, pH 4.5. After washing the column, bound protein was eluted with a linear NaCl gradient (from 0 to 0.25 M NaCl). Fractions from the column were analysed for pectin esterase activity. The major part of the pectin esterase activity eluted in one peak, the peak fractions were pooled.

Ammonium sulphate (AMS) was added to the pool to a final AMS concentration of 1.6 M and the enzyme was added to a 40 ml Phenyl Toyopearl column equilibrated in 100 mM H$_3$BO$_3$, 10 mM DMG, 2 mM CaCl$_2$, 1.6 M AMS, pH 7.0. After washing the column, bound protein was eluted with a linear AMS gradient (from 1.6 to 0 M AMS). The buffer of the pectin esterase peak was exchanged for 25 mM CH$_3$COOH/NaOH, pH 4.5 by a pass on a 1.4L G25 Sephadex column equilibrated in 25 mM CH$_3$COOH/NaOH, pH 4.5.

The pectin esterase enzyme was applied to a 50 ml S-Sepharose HP column equilibrated in 25 mM CH$_3$COOH/NaOH, pH 4.5. After washing the column, bound protein was eluted with a linear NaCl gradient (from 0 to 0.1 M NaCl). Fractions with pectin esterase activity were analysed by SDS-PAGE. The fractions contained one band only.

Electrophoresis

SDS-PAGE electrophoresis was performed in a Mini-Leak 4 electrophoresis unit (Kem-En-Tec, Denmark) as a modified version of the Laemli procedure (Laemmli (1970) Nature 227:680–6.85). Gels were coomassie stained according to the manufacturer's instructions.

Isolation of the DNA Sequence Shown in SEQ ID No. 1

The pectin esterase encoding part of the DNA sequence shown in SEQ ID No. 1 coding for the pectin esterase of the invention can be obtained from the deposited organism *Escherichia coli* DSM 10357 by extraction of plasmid DNA by methods known in the art (Sambrook et al. (1989) Molecular cloning: A laboratory manual, Cold Spring Harbor lab., Cold Spring Harbor, N.Y.).

Hybridization

Suitable hybridization conditions for determining hybridization between a nucleotide probe and an "analogous" DNA sequence of the invention may be defined as described below. The oligonucleotide probe to be used is the DNA sequence corresponding to the pectin esterase encoding part of the DNA sequence shown in SEQ ID NO 1, i.e. nucleotides 4–933 in SEQ ID No. 1.

Hybridization Conditions

The hybridization conditions referred to herein to define an analogous DNA sequence as defined in part b) of the first aspect of the invention which hybridizes to the pectin esterase encoding part of the DNA sequence shown in SEQ ID NO 1, i.e. nucleotides 4–933, under at least low stringency conditions, but preferably at medium or high stringency conditions are as described in detail below.

Suitable experimental conditions for determining hybridization at low, medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) *Anal. Biochem.* 132:6–13), $^{32}$P-dCTP-labeled (specific activity>1×10$^9$ cpm/µg) probe for 12 hours at ca. 45° C. The filter is then washed twice for 30 minutes in 2×SSC, 0.5% SDS at least 55° C. (low stringency), more preferably at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

Immunological Cross-reactivity

Antibodies to be used in determining immunological cross-reactivity may be prepared by use of a purified pectin esterase. More specifically, antiserum against the pectin esterase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation (($NH_4$)$_2SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Media

YPD: 10 g yeast extract, 20 g peptone, $H_2O$ to 900 ml. Autoclaved, 100 ml 20% glucose (sterile filtered) added.

YPM: 10 g yeast extract, 20 g peptone, $H_2O$ to 900 ml. Autoclaved, 100 ml 20% maltodextrin (sterile filtered) added.

10×Basal salt: 75 g yeast nitrogen base, 113 g succinic acid, 68 g NaOH, $H_2O$ ad 1000 ml, sterile filtered.

SC-URA: 100 ml 10×Basal salt, 28 ml 20% casamino acids without vitamins, 10 ml 1% tryptophan, $H_2O$ ad 900 ml, autoclaved, 3.6 ml 5% threonine and 100 ml 20% glucose or 20% galactose added.

SC-agar: SC-URA, 20 g/l agar added.

PEG 4000 (polyethylene glycol, molecular weight=4,000) (BDH, England)

1% apple pectin DE 75% (Herbstreith, Germany)

1% HSB agarose (FMC Litex A/S, Denmark)

MTAB (mixed alkyltrimethylammonium bromide) (Sigma)

EXAMPLES

Example 1

Cloning and Expression of a Pectin Esterase from *Meripilus giganteus* CBS 521.95 mRNA was isolated from *Meripilus giganteus*, CBS No. 521.95, grown in cellulose-containing fermentation medium with agitation to ensure sufficient aeration. Mycelia were harvested after 3–5 days' growth, immediately frozen in liquid nitrogen and stored at −80° C. A library from *M. giganteus*, CBS No. 521.95, consisting of approx. $10^6$ individual clones was constructed in *E. coli* as described with a vector background of 1%. Plasmid DNA from some of the pools was transformed into yeast, and 50–100 plates containing 250–400 yeast colonies were obtained from each pool.

Pectin esterase-positive colonies were identified and isolated on SC-agar plates with the apple pectin assay. cDNA inserts were amplified directly from the yeast colonies and characterized as described in the Materials and Methods section above. The DNA sequence of the cDNA encoding the pectin esterase is shown in SEQ ID No. 1 and the corresponding amino acid sequence is shown in SEQ ID No. 2. In SEQ ID No. 1 DNA nucleotides from No 4 to No. 933 define the pectin esterase encoding region.

The cDNA is obtainable from the plasmid in DSM 10357.

Total DNA was isolated from a yeast colony and plasmid DNA was rescued by transformation of *E. coli* as described above. In order to express the pectin esterase in Aspergillus, the DNA was digested with appropriate restriction enzymes, size fractionated on gel, and a fragment corresponding to the pectin esterase gene was purified. The gene was subsequently ligated to pHD414, digested with appropriate restriction enzymes, resulting in the plasmid pA2PE18.

After amplification of the DNA in *E. coli* the plasmid was transformed into *Aspergillus oryzae* as described above.

Test of *A. oryzae* Transformants

Each of the transformants were tested for enzyme activity as described above. Some of the transformants had pectin esterase activity which was significantly larger than the *Aspergillus oryzae* background. This demonstrates efficient expression of the pectin esterase in *Aspergillus oryzae*.

Example 2

Homology to Published Pectin Esterases

A homology search with the pectin esterase of the invention against nucleotide and protein databases was performed. The homology search showed that the most related pectin esterases was a pectin esterase from *Aspergillus aculeatus* and a pectin esterase from *Aspergillus tubigensis* (previously said to be from *A. niger*).

According to the method described in the "DETAILED DESCRIPTION OF THE INVENTION" the DNA homology of the pectin esterase of the invention against most prior art pectin esterases was determined using the computer program GAP. The pectin esterase of the invention has only 54% DNA homology to the pectin esterase from *Aspergillus aculeatus* (WO 94/25575) and the pectin esterase of the invention has only 56% DNA homology to the pectin esterase from *Aspergillus tubigensis* (Khanh et al. (1990) "Nucleotide and derived amino acid sequence of a pectinesterase cDNA isolated from *Aspergillus niger* strain RH5344", Nucleic Acids Res. 18:4262; Khanh et al. (1991) "Characterization and expression of a genomic pectin methyl esterase-encoding gene in *Aspergillus niger*", Gene 106:71–77).

According to the method described in the "DETAILED DESCRIPTION OF THE INVENTION" the polypeptide homology of the pectin esterase of the invention against most prior art pectin esterases was determined using the computer program GAP. The pectin esterase of the invention has only 47% polypeptide homology to the pectin esterase from *Aspergillus aculeatus* and the pectin esterase of the invention has only 44% polypeptide homology to the pectin esterase from *Aspergillus tubigensis*.

This shows that the pectin esterase of the invention indeed is distant from any known pectin esterases.

Example 3

Purification and Characterization of the Recombinant Pectin Esterase of the Invention The pectin esterase was produced by fed batch fermentation of *A. oryzae* expressing the enzyme as described in Materials and Methods above.

The recombinant pectin esterase was purified and characterized by the methods described in the Materials and Methods section above. The molecular weight of the enzyme was determined to 37 kDa by SDS-PAGE.

Example 4

In Situ Gelation of Strawberry Jam Free Methanol as an Indication of the Gelifying Properties Materials and Methods Pectinesterase batch PPJ 4300, 423 PEU/g Pectinesterase: *Meripulus giganteus*, 2,4 PEU/g Strawberries, frozen, sort: Senga sengana The activity of the pectinesterase is given in Pectin-Esterase-Units (PEU) defined as the amount of enzyme which under standardised conditions liberates 1 mmol carboxyl groups per minute (Novo Nordisk assay ABT-SM-0005.02.1, Available upon request from Novo Nordisk A/S).

Jam Preparation

The preparation of the jam is carried out according to the standard procedure for jam preparation (Novo Nordisk Standard Operation Procedure, ABF-SP-4002.02/01, Available upon request from Novo Nordisk A/S).

A 300 g portion of jam was prepared. The ratio of strawberry and sugar was: 180 g berries+120 g sugar. After an initial pre-cooking the fruit slurry was divided into 2×3—50 g portions, the samples were cooled to 40° C. and enzyme was added as follows:

1) control with no enzyme added
2) PE, PPJ 4300, 10 PEU/kg fruit
3) PE, *Meripulus giganteus*, 10 PEU/kg fruit The samples were sealed and allowed to stand for 1 hour, then the samples were heat treated for 3 min at 90° C. in order to inactivate the enzyme.

In the present trials the quantification of free methanol was carried out at Alfred Jørgensens Lab. A/S, Copenhagen. The samples were initially destilled, then analysed using a capillary gaschromatograph in combination with mass spectrometry detection.

Results and Discussion

The results appears from Table 1 below:

TABLE 1

| Methanol formation | |
|---|---|
| | Methanol, ppm |
| Control | 12 ppm |
| PE, PPJ 4300, 10 PEU/kg fruit | 200 ppm |
| PE, *M. gig.*, 10 PEU/kg fruit | 340 ppm |

It is clearly demonstrated that pectinesterase from *Meripulus giganteus*, resulting in 340 ppm free methanol, is superior to the more traditional Aspergillus derived PE, resulting in a free methanol formation of 200 ppm.

If the pectin content of strawberries is estimated to 0.6% and the degree of esterification (DE) is estimated to 70%, it can be calculated, that the final DE of the traditional PE product results in a DE of 52, while *Meripulus giganteus*—PE results in a DE of 38.

The degree of esterification is of importance for the textural characteristics of in situ gelated jam and also for other PE modified vegetable products. The degree of esterification determines the number of Ca-bridges that can be formed and is thus related to the gel strength or the viscosity of a certain product.

It is thus obvious that the *Meripulus giganteus* derived enzyme is a useful tool in creating strong and useful gels. The enzyme is probably also as an even stronger alternative to the chemical modification of extracted pectins, than the traditional Aspergillus derived PE product.

---

What is claimed is:

1. DNA construct comprising a DNA sequence encoding an enzyme exhibiting pectin esterase activity, wherein said sequence is selected from the group consisting of:
   (a) a pectin esterase-encoding part of the DNA sequence cloned into plasmid pYES 2.0 present in *E. coli* DSM 10357;
   (b) a DNA sequence corresponding to nucleotides 4–933 of SEQ ID NO: 1; and
   (c) a DNA sequence which
      i) is at least 70% homologous with the DNA sequence defined in (a) or (b), wherein said homology is determined using GAP, with a GAP creation penalty of 5.0 and a GAP extension penalty of 0.3; or
      ii) hybridizes with the DNA sequence shown in positions 4–933 in SEQ ID NO 1 at medium stringency, or
      iii) encodes a polypeptide which is at least 60% homologous with the polypeptide encoded by a DNA sequence comprising the DNA sequence defined in (a) or (b), wherein said homology is determined using GAP, with a GAP creation penalty of 3.0 and a GAP extension penalty of 0.1.

2. The DNA construct according to claim 1, wherein said sequence is derived from a microorganism selected from the group consisting of a filamentous fungus, a yeast, and a bacteria.

3. The DNA construct according to claim 2, wherein said sequence is derived from a strain of *Meripilus giganteus*.

4. The DNA construct according to claim 3, wherein said sequence is derived from *Meripilus giganteus* CBS 521.95.

5. The DNA construct according to claim 2, wherein said microorganism is selected from the group consisting of Aspergillus, Saccharomyces, Bacteroides, Erwinia, Pseudomonas, and Clostridium.

6. The DNA construct according to claim 1, in which the DNA sequence is derived from *Escherichia coli* DSM 10357.

7. A recombinant vector comprising a DNA construct according to claim 1.

8. A cell comprising a vector according to claim 7.

9. The cell according to claim 8, wherein said cell is a eukaryotic cell selected from the group consisting of a yeast cell or a filamentous fungal cell.

10. The cell according to claim 9, wherein said cell is selected from the group consisting of Fusarium, Aspergillus, Saccharomyces, Meripilus, and Trichoderma.

11. The cell according to claim 10, wherein said cell is selected from the group consisting of *Fusarium graminearum, Fusarium cerealis, Aspergillus niger, Aspergillus oryzae, Trichoderma harzianum*, and *Trichoderma reesei*.

12. The cell according to claim 9, wherein said cell is *Meripilus giganteus* CBS No. 521.95.

13. The cell according to claim 9, wherein said cell is *Saccharomyces cerevisiae*.

14. A method of producing an enzyme exhibiting pectin esterase activity, the method comprising (i) culturing a cell according to claim 8 under conditions permitting the production of the enzyme, and (ii) recovering the enzyme from the culture.

15. An isolated cell, wherein said cell is *Escherichia coli* DSM 10357.

16. An isolated cell, wherein said cell is *Meripilus giganteus* CBS 521.95.

* * * * *

SEQUENCE LISTING

<160> NUMBER OF SEQ ID NOS: 2

<210> SEQ ID NO 1
<211> LENGTH: 1128
<212> TYPE: DNA
<213> ORGANISM: Meripilus giganteus

<400> SEQUENCE: 1

```
agaatgcagt cccacttgtt cttgctgttc tcttacctca tcgcctgtgc gtctgcgctc      60
agcagtccgc ctgcaggcgc aatcaccgtc ggctccggtg gcaagtattc aacgttgtcc     120
gcagccctca aggacacgtc gagctccgtc tacttcgtgt tctccgggac atacacggac     180
accgcgatta ttactcggcc gaacgtgaag gtgtacgggc agacgaacac accgtcgtcc     240
tataccggca atactgtcac catcaccaat aacattccgg cctccaaggc gggctccaat     300
gatgcgagcg ggacggtgca agtgcacgcc gagaacgtgt cactctacaa cctaaacatc     360
```

```
gcgaacacgt acggcaagac agtcgaccag gcgcaagcga tcgcactgag cgtgcaggcg    420
ggccagttcg gcgcatacgg actcaagatt acggggggacc aggacaccct cctagctaac    480
```

```
gcgaacacgt acggcaagac agtcgaccag gcgcaagcga tcgcactgag cgtgcaggcg    420
ggccagttcg gcgcatacgg actcaagatt acgggggacc aggacaccct cctagctaac    480
gtcggcgcgc aatactatgc gaacagctgg atagaaggcg ctgtggactt catattcggg    540
atgcaagcct cgatctggat cacccgctcg gtcatcaaca cgatcgggag cgggtgcatc    600
accgcgtcgg ggcgctcgag taacgacggc ttctggtatg tcatcgacag ctcgaccgtg    660
cagggcaccg ggacggcgta cctcgggcgc cctggcgcg actacgcgcg cgtcgtgttc    720
cagaagagca cgctcgggag caacgtgccc gcggccggct ggtcgatttg aacgtcggc    780 accccgcaga ccgaccatgt cacgttcgcc gagtacggga acaccggccc cggcgcgtcc    840
ggcacgcgcg cgagcttcag cacgaagctg tccgcgccgg tcgcgatcaa gacggtgctg    900
aactcgacga gctggatcga ccccgccttc ctctgacccc gccgacggca cgacaaacg    960 agagagagcg agggcagcag agggacgagt gccgagtgcc ggtgcggctg agggctatga   1020
cgtcgatcga tggtcggctt gacgtcgttg tacacgtacg gatgcagtca tcgaacgttc   1080
ggttgcgact tgccaaaaaa aaaaaaaaaa aaaaaaaaaa aaaaaaaa                1128

<210> SEQ ID NO 2
<211> LENGTH: 310
<212> TYPE: PRT
<213> ORGANISM: Meripilus giganteus

<400> SEQUENCE: 2

Met Gln Ser His Leu Phe Leu Phe Ser Tyr Leu Ile Ala Cys Ala
 1               5                   10                  15

Ser Ala Leu Ser Ser Pro Pro Ala Gly Ala Ile Thr Val Gly Ser Gly
                20                  25                  30

Gly Lys Tyr Ser Thr Leu Ser Ala Ala Leu Lys Asp Thr Ser Ser Ser
            35                  40                  45

Val Tyr Phe Val Phe Ser Gly Thr Tyr Thr Asp Thr Ala Ile Ile Thr
        50                  55                  60

Arg Pro Asn Val Lys Val Tyr Gly Gln Thr Asn Thr Pro Ser Ser Tyr
65                  70                  75                  80

Thr Gly Asn Thr Val Thr Ile Thr Asn Asn Ile Pro Ala Ser Lys Ala
                85                  90                  95

Gly Ser Asn Asp Ala Ser Gly Thr Val Gln Val His Ala Glu Asn Val
            100                 105                 110

Ser Leu Tyr Asn Leu Asn Ile Ala Asn Thr Tyr Gly Lys Thr Val Asp
        115                 120                 125

Gln Ala Gln Ala Ile Ala Leu Ser Val Gln Ala Gly Gln Phe Gly Ala
    130                 135                 140

Tyr Gly Leu Lys Ile Thr Gly Asp Gln Asp Thr Leu Leu Ala Asn Val
145                 150                 155                 160

Gly Ala Gln Tyr Tyr Ala Asn Ser Trp Ile Glu Gly Ala Val Asp Phe
                165                 170                 175

Ile Phe Gly Met Gln Ala Ser Ile Trp Ile Thr Arg Ser Val Ile Asn
            180                 185                 190

Thr Ile Gly Ser Gly Cys Ile Thr Ala Ser Gly Arg Ser Ser Asn Asp
        195                 200                 205

Gly Phe Trp Tyr Val Ile Asp Ser Ser Thr Val Gln Gly Thr Gly Thr
    210                 215                 220

Ala Tyr Leu Gly Arg Pro Trp Arg Asp Tyr Ala Arg Val Val Phe Gln
225                 230                 235                 240
```

```
Lys Ser Thr Leu Gly Ser Asn Val Pro Ala Ala Gly Trp Ser Ile Trp
            245             250                 255

Asn Val Gly Thr Pro Gln Thr Asp His Val Thr Phe Ala Glu Tyr Gly
            260             265                 270

Asn Thr Gly Pro Gly Ala Ser Gly Thr Arg Ala Ser Phe Ser Thr Lys
            275             280                 285

Leu Ser Ala Pro Val Ala Ile Lys Thr Val Leu Asn Ser Thr Ser Trp
    290             295                 300

Ile Asp Pro Ala Phe Leu
305             310
```